United States Patent [19]
Lurie

[11] Patent Number: 6,090,788
[45] Date of Patent: Jul. 18, 2000

[54] PHOTOTHERAPY BASED METHOD FOR TREATING PATHOGENS AND COMPOSITION FOR EFFECTING SAME

[75] Inventor: Raz Lurie, Tel Aviv, Israel

[73] Assignee: Dermatolazer Technologies Ltd., Tel Aviv, Israel

[21] Appl. No.: 09/343,199

[22] Filed: Jun. 30, 1999

Related U.S. Application Data

[63] Continuation of application No. PCT/US98/14162, Jul. 13, 1998.
[51] Int. Cl.⁷ ..................................................... A61K 31/70
[52] U.S. Cl. ............................ 514/23; 427/595; 427/596; 606/2; 606/3
[58] Field of Search ................... 514/23, 557; 427/78.04, 427/595, 596; 606/2, 3

[56] References Cited

U.S. PATENT DOCUMENTS

| | | | |
|---|---|---|---|
| 5,597,559 | 1/1997 | Olejnik et al. | 424/78.04 |
| 5,648,389 | 7/1997 | Gans et al. | 514/557 |
| 5,925,178 | 7/1999 | Martin et al. | 106/31.65 |

*Primary Examiner*—Elli Peselev
*Attorney, Agent, or Firm*—Mark M. Friedman

[57] ABSTRACT

A method for treating an area of skin or nail affected with a pathogen, the method comprising the step of irradiating the area of skin or nail with a light beam having at least one wavelength absorbable by the pathogen.

23 Claims, 2 Drawing Sheets

PHOTOTHERAPY BASED METHOD FOR TREATING PATHOGENS AND COMPOSITION FOR EFFECTING SAME

This is a continuation of PCT/US98/14162, filed Jul. 13, 1998.

FIELD AND BACKGROUND OF THE INVENTION

The present invention relates to a phototherapy based method for treating pathogens and to a pharmaceutical composition for effecting same. More particularly, the present invention relates to a laser based method and a pharmaceutical composition for treating nail and skin associated pathogens, such as fungi, yeast, bacteria, and viruses which cause nail and skin infections.

The nails, which are thin horny plates consisting of modified epidermis growing on the upper side of the end of the digits (fingers or toes), serve many useful functions, such as protecting the digits, enhancing fine touch, and increasing tactile sensitivity.

The nails are essential for picking up small objects and for performing fine activities such as fastening a button. The nails provide an excellent tool for scratching and can be used as both offensive and defensive weapons. Furthermore, being external and exposed, the nails serve as an important aesthetic attribute.

Thus, any condition that adversely affects one or more of the nails may have deleterious consequences, affecting not only a person's ability to perform some delicate and other daily tasks, but potentially adversely affecting his or her quality of life in a broader sense.

Onychomycosis is a general infection of the nail unit caused by fungal microorganisms such as dermatophytes, yeasts, and nondermatophyte molds. The term tinea unguium refers to dermatophytic infection of a nail unit.

Onychomycosis may affect toe nails as well as fingernails, and may lead to onycholysis (separation of nail plate from the nail bed), subungual debris or hyperkeratosis, discoloration of the nail plate, partial or complete destruction of the nail plate, and thickening of the nail plate, leading to both functional and aesthetic problems [Farmer et al. (1996) Guidelines of care for superficial mycotic infections of the skin: onychomycosis. J. Am. Acad. Dermatol. 34:116–121].

Onychomycosis occurs worldwide and its incidence has been steadily increasing [Daniel (1991) The diagnosis of nail fungal infection. Arch. Dermatol. 127:1566–1567]. Nail disorders comprise approximately 10% of all dermatologic conditions [Farmer et al. (1996) Guidelines of care for nail disorders. J. Am. Acad. Dermatol. 34:329–533]. Up to 50% of all nail disorders are caused by fungal infections [Achten and Wanet-Rouard (1978) Onychomycosis in the laboratory. Mykosen 23:125–127; and Andre and Achten (1987) Onychomycosis. Int. J. Dermatol. 26:481–490].

Onychomycosis is often considered an age-related infection. In some populations, as many as 15% to 20% or more of individuals between the ages of 40 and 60 years of age are affected by onychomycosis [Zaias (1985) Onychomycosis. In: Daniel C. R. III, Ed. Dermatologic clinics. Philadelphia: WB Saunders Co. pp. 445–460].

In 1989, Rosenbach and Schneider conducted a comprehensive study to evaluate the overall costs of onychomycosis in the Medicare population (e.g., >65 years of age) of the U.S. [Scher (1996) Onychomycosis: A significant medical disorder. J. Am. Acad. Dermatol. 35 (supp.):2–5]. The results revealed that, during a twelve month period, between 1989 and 1990, a total of 662,000 patients had made 1,300,000 visits to a physician because of a primary complaint of onychomycosis. At the time this study was conducted the costs associated with these visits exceeded $43 million.

Various factors are considered to cause the reported increase in onychomycosis cases. These include (i) growing population of elderly people; (ii) spread of HIV infections (AIDS), which affect immune capabilities; (iii) increased use of therapeutic interventions resulting in immunosuppression; (iv) "health craze", (v) use of occlusive clothing and shoes; (vi) extensive and prolonged sweating associated with vigorous physical activities such as tennis, paddle ball, etc.; and (vii) communal bathing facilities.

People affected with onychomycosis may suffer various physiological and psychological consequences.

The physiological consequences associated with onychomycosis may include (i) limitations in mobility due to pain; (ii) reduced peripheral circulation and, as a result, slow healing thereat; (iii) exacerbation of the diabetic foot; (iv) recurrent thrombophlebitis and cellulitis; and (v) creation of a fungal reservoir, which may trigger urticaria; bacterial infections; pain; and dermatophytic reactions.

The psychological consequences associated with onychomycosis may include (i) embarrassment; (ii) low self-consciousness; (iii) loss of self-esteem; (iv) loss of self-confidence; (v) anxiety; (vi) depression contagion; (vii) social effects; (viii) impaired relationships; and in some cases even (ix) avoidance of intimacy; all depending, of course, on the specific affected individual and its psychological profile. Individuals of the females gender are probably more susceptible to the psychological consequences associated with onychomycosis, especially of the fingernails.

Figure 1:
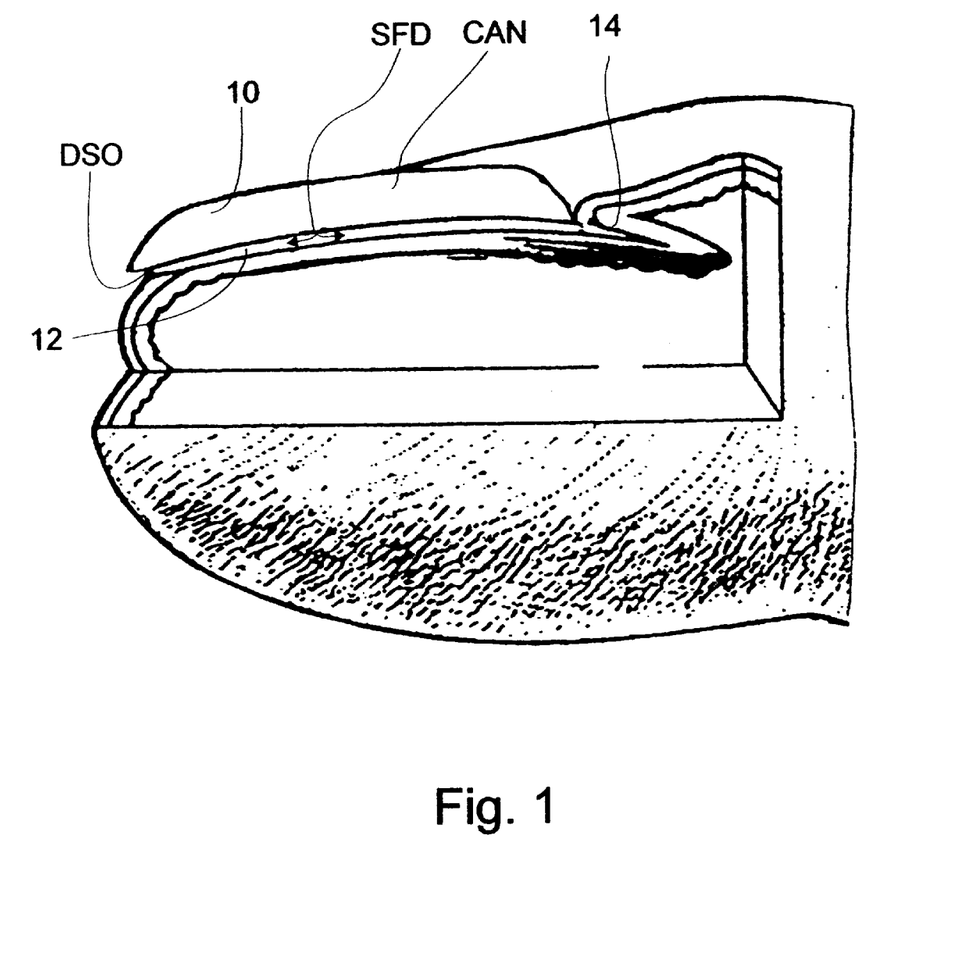
FIG. 1 is a cross sectional view of a toe nail.

With reference to FIG. 1, presented is a human toe nail having a plate 10 a nail bed 12 and a matrix or growth origin 14. There are four major types of fungal nail infections: distal subungual onychomycosis (DSO), proximal subungual onychomycosis (PSO), white superficial onychomycosis (SFO) and Candida onychomycosis (CAN). The affected regions are marked in FIG. 1. Each of the four types of fungal nail infections is differentiated on the basis of the pattern of fungal invasion into the nail plate and by the causative pathogen.

In the most common form of onychomycosis, distal subungual, the fungus (typically *Trichophyton rubrum*) invades distally in the area of the hyponychium.

In proximal subungual onychomycosis, the fungus (again, typically *T. rubrum*) invades under the cuticle and spreads distally from the proximal nail bed region.

In white superficial onychomycosis, the fungus (typically *T. mentagrophytes* or certain molds, such as various Fusarium sp.) directly invades the nail plate.

Candida onychomycosis occurs in patients with chronic mucocutaneous candidiasis and involves invasion of the entire nail plate by Candida organisms (typically *C. albicans*)

There are three major groups of fungi that cause onychomycosis. These are dermatophytes, yeasts, and non-dermatophyte molds. However, dermatophytes remain, by far, the most common pathogens associated with onychomycosis. The largest study in the field [Summerbell et al. (1989) Onychomycosis, tinea pedis and tinea manuum caused by nondermatophytic filamentous fungi. Mycoses 32:609–619] revealed that in more than 3,000 studied nails, 91% of fungal infections were caused by dermatophytes, 6% by Candida sp.; and 3% by nondermatophyte molds (primarily *Scopulaiopsis brevicaulis*). In the dermatophyte group, in 70% of the cases studied the causative pathogen was *Trichophyton rubrum*, in 20% *T mentagrophytes* and in 10% other pathogens [Brener (1996) Nail and hair. Dyonon, Tel Aviv University, p. 43].

Elewski [Elewski (1996) Diagnostic techniques for confirming onychomycosis. J. Am. Acad. Dermatol. 35 (supp.):6–9] findings are similar, wherein 90% of fungal nail infections studied were found to be caused by dermatophytes; 7% by Candida sp.; and 3% by nondermatophyte molds.

A study by Clayton in the United Kingdom [Clayton (1992) Clinical and mycological diagnostic aspects of onychomycosis and dermatomycosis. Clin. Exp. Dermatol. 17 (supp. 1):37–40] showed that, of 699 specimens, 81% of nail infections were caused by dermatophytes, 17% by yeasts, and 2% by nondermatophyte molds.

The common dermatophyte species associated with onychomycosis, their associated pathogenicity, growth rates and colonies morphology when grown in culture are listed below. The morphology of culture grown colonies of a studied pathogen, in many cases, serves as a diagnostic tool.

*Trichophyton rubrum*
Pathogenicity: Typically infects the skin and nails. Rarely infects the beard, hair, or scalp. *T. rubrum* is presently the most common dermatophyte to infect human beings.
Rate of growth: Slow. Maturation within 14 days.
Morphology and color of colony: Surface of colony is granular or fluffy, white to buff. Reverse (i.e., viewed from underneath) is deep red or purplish, occasionally brown, yellow, orange, or even colorless. Pigment production is best seen when colonies are grown in culture in presence of cornmeal or potato dextrose containing agar. The pigment responsible for the color of *Trichophyton rubrum* colonies is carotene. For action during arthoroconidia formation see Rippon (1982) "Medical Mycology", W. B. Saunders Company. p. 213. The pigment is slow in developing. The color is yellow initially, developing through a Melanoid-green, and finally becoming red. Several pigments are formed by *Trichophyton rubrum* at different times. A black melanin like pigment is sometimes produced. This is the var. nigricans [Rippon (1988) "Medical Mycology", W. B. Saunders Company. p. 257].

*Trichophyton mentagrophytes*
Pathogenicity: Invades all parts of the body surface, including hair and nails. *T. mentagrophytes* is the most common causative pathogen associated with athlete's foot.
Rate of growth: Moderate. Maturation within 7–10 days.
Morphology and color of colony: Varies greatly. Surface may be buff and powdery or white and downy. May develop a pinkish or yellowish color. The powdery form exhibits concentric and radial folds. Colonies rapidly develop a dense fluff with little or no conidiation. Reverse is usually brownish tan but may be colorless, yellow, or red.

*Epidermophyton floccosum*
Pathogenicity: Produces infection in skin and nails. Does not infect hair.
Rate of growth: Moderate. Maturation within 10 days.
Morphology and color of colony: Surface is brownish-yellow to olive-gray or khaki. At first it is lumpy and sparse and then folded in center and grooved radially, becoming velvety. After several weeks, fluffy white sterile mycelium covers the colony. Reverse is orange to brownish, sometimes with a thin yellow border.

*Trichophyton tonsurans*
Pathogenicity: The principle etiologic agent of scalp ringworm in the United States. Also infects the skin and nails.
Rate of growth: Moderately slow. Maturation within 12 days.
Morphology and color of colony: Highly variable. Surface may be white, gray, yellow, rose, or brown. Surface is usually suedelike, with many radial or concentric folds. Reverse is usually reddish-brown (pigment may diffuse into the medium). Sometimes it is yellow or colorless.

*Trichophyton violaceum*
Pathogenicity: Infects the scalp, hair, skin, and nails.
Rate of growth: Slow. Maturation within 14–21 days.
Morphology and color of colony: Original cultures are waxy, wrinkled, heaped, and characterized by a deep purplish-red color. Subcultures are more downy, and they decrease in color. Reverse color is lavender to purple.

*Trichophyton schoenleini*
Pathogenicity: Causes favus, a chronic, scarring scalp infection that results in permanent hair loss. Sometimes infects the nails and skin.
Rate of growth: Slow. Maturation within 15 days.
Morphology and color of colony: Colony is whitish, waxy, or slightly downy; heaped or folded; and sometimes yeast-like. Growth is often submerged in the agar. Reverse is colorless or yellowish orange to tan.

*Trichophyton verrucosum*
Pathogenicity: Infects scalp, beard, nails, and skin of various parts of the body. Usually contracted from cattle.
Rate of growth: Slow. Maturation within 14–21 days. Unlike other dermatophytes, this fungus grows best at 37° C.
Morphology and color of colony: Usually small, heaped and buttonlike but sometimes flat. Texture skinlike, waxy, or slightly downy. Usually white, but can be gray or yellow. Reverse varies from nonpigmented to yellow.

*Microsporum ferrugineum*
Pathogenicity: Primarily causes ringworm of the scalp (tinea capitis) in children. Also known to infect the skin and nails.
Rate of growth: Slow. Maturation within 12–20 days.
Morphology and color of colony: Surface is usually yellow to rusty orange, smooth, waxy, heaped; may be flatter and develop a white velvety fuzz. Reverse is creamish to brownish. During repeated subculturing, the colonies often lose their pigment.

*Microsporum canis* var. *canis*
Pathogenicity: Causes infections of scalp and skin. Most prevalent in children. Has occasionally been reported to cause nail infection. Most infections in humans are acquired from infected dogs or cats.
Rate of growth: Moderate. Maturation within 6–10 days.
Morphology and color of colony: Surface is whitish, coarsely fluffy, with yellow pigment at the periphery and closely spaced radial grooves. Reverse is deep yellow and turns brownish-yellow with age.

The common Candida species associated with onychomycosis, their associated pathogenicity, growth rates and colonies morphology in culture are listed below.

*Candida albicans*
Pathogenicity: Most common cause of candidiasis (also known as candidosis), which is an acute, subacute, or chronic infection involving any part of the body. This organism may also be found as normal flora in the skin, mouth, vaginal mucous membranes, and stools.
Rate of growth: Rapid. Maturation within 3 days.
Morphology and color of colony: Cream colored, pasty, smooth.

*Candida tropicalis*
Pathogenicity: As is the case for many species of Candida and other yeasts, *C. tropicalis* is known to cause infection, especially in immunocompromised, predisposed patients. It is also found without evidence of a disease.
Rate of growth: Rapid. Maturation within 3 days.
Morphology and color of colony: Creamy with mycelial fringe.

*Candida parapsilosis*
Pathogenicity; This species has been known to cause infections in particularly susceptible individuals. It is a relatively frequent cause of candidal endocarditis.
Rate of growth: Rapid. Maturation within 3 days.
Morphology and color of colony: Creamy, sometimes developing a lacy appearance.

The common Mold species associated with onychomycosis, their associated pathogenicity, growth rates and colonies morphology when grown in culture are listed below.

Scopulariopsis spp.
Pathogenicity: Commonly considered a contaminant, but is known to infect the nails (usually toe nail) and is rarely associated with infection of soft tissue, bone, and lungs in immunocompromised patients.
Rate of growth: Rapid. Maturation within 5 days.
Morphology and color of colony: Surface is at first white and glamorous and then usually becomes powdery light brown with a light tan periphery. Some rarely encountered species may be very dark. Reverse is tan with brownish center.

Fusarium spp.
Pathogenicity: Commonly considered a contaminant, but known to be a relatively frequent agent of mycotic eye infections. It is occasionally involved in myvetoma, sinusitis, skin and nail infections, and disseminated systemic infections in severely debilitated hosts. Disease has also been reported in individuals after ingestion of food prepared from grains that have been overgrown by toxin producing species.
Rate of growth: Rapid. Maturation within 4 days.
Morphology and color of colony: At first the colony is white and cottony, but it often quickly develops a pink or violet center with a lighter periphery. Some species remain white or become tan. Reverse is light in color.

Pigments produced by various molds, fungi and bacteria in different developmental stages and as a response to an inducer (e.g., nutrient, radiation, temperature, etc.) include, but are not limited to, aspergillin, aurantin, aurofusarin, boletol, carotennoids, catenarin, chrysogenin, citrinin, citromycetin, cynodontin, erythroglaucin, flavoglaucin, fulvic acid, helminthosporin, monascoflavin, monascorubin, ochracin, ousporin, pheonicin, physcion, ravenelin, rubrofusarin, melanin, and tritsporin [Salle (1948) "Fundamental Principles of Bacteriology", McGraw-Hill book company, New York].

The colors associated with cultured colonies is induced by various growth conditions, including, but not limited to nutrients, temperature and irradiation. Since when grow as parasites the above fungi typically do not develop colors, diagnostic techniques for confirming onychomycosis were developed. These include direct microscopy, fungal culturing (as described), nail histopathology, immunohistochemistry and flow cytometry.

The treatment for onychomycosis has been disappointing because of its duration, poor response rate, side effects and high incidence of recurrence. Treatment for onychomycosis may be divided to nonpharmacological approaches, topical antifungal agents and oral therapy.

Nonpharmacological approaches: Various nonpharmacological approaches are used to manage nail fungal infections, including buffing or filing of the nails, nail avulsion or debridement, and the use of surgery and/or various chemicals and solutions to remove the nail plate. These procedures are uncomfortable and probably do not reduce the likelihood of relapse. In addition, they may permanently alter the shape of the nail unit and lead to persistent non attachment of the nail plate to the nail bed (onycholysis) and increase the likelihood of ingrown nails. Chemical removal of dystrophic nails should be reserved for patients with onychogryphosis or very thick nails, or for painful nails in patients who cannot undergo surgery. Unfortunately ,these methods do not "cure" the infection, but only keep the worst aspects of the disease under some control.

Topical antifungal agents: Numerous topical antifungal agents (creams, lotions, solutions, powders and sprays) are used for the empirical management of onychomycosis. It is widely agreed that these preparations are largely ineffective, even when used in conjunction with nail avulsion. The experience with the newer topical solutions, such as nail lacquers (e.g., amorolfine) is inconclusive.

Some traditional topical antifungal agents are used to treat dermatophyte infections. These include azoles (ketoconazole, clotrimazole, sulconazole, oxiconazole and econazole) with or without urea, Whitefield's ointment, potassium permanganate, ciclopirox olamine, amorolfine, allylamines (naftifine, terbinafine), organic acids (salicylic, undecylenic), halogenated phenolic esters (haloprogin), thiocarbamate derivatives (tolnaftate), and polyenes (nystatin) which are not effective against dermatophytes.

A combination of a nonpharmacologic approach and a topical antifungal agents is disclosed in SU 1801519 A to Abramovitch et al., wherein following the removal of the onychomycosial nail plate, the nail bed is treated by a fungicidal preparation and further by recurrent (25–30 sessions) irradiations of the nail bed by a low density (1–2 $mW/cm^2$) red laser beam.

Oral therapy: The two oral antifungal drugs that have traditionally comprised the mainstay of the treatment of onychomycosis are griseofulvin and ketoconazole. These two oral anti fungal agents have been used for the treatment of onychomycosis for almost half a century. One of the major limitations of treatment with either griseofulvin or ketoconazole is the long duration of therapy required. In addition, the clinical and mycological cure rates are low, and there is a greater than 75% probability that the patient will relapse within two years. The potential for significant side effects is another problem, particularly with ketoconazole.

The new generation orally administered antifungal agents are fluconazole and itraconazole. Itraconazol adverse effects include nausea, abdominal pain, vomiting, diarrhea, anorexia, headaches, dizziness, rash, pruritus, fatigue, fever, elevation of liver test and hepatic injury. Fluconazole adverse effects include nausea, abdominal pain, vomiting, diarrhea, elevation of liver test and hepatic injury.

Orally administered allylamines, such as terbinafine and naftifine, adverse effects include gastrointestinal irritation, dyspepsia, stomachache, gastritis, fullness, nausea, vomiting, diarrhea, hepatobiuary dysfunction including hepatitis, skin reactions, urticaria rash. When administered it becomes essential to monitor liver functions.

When orally administering any of these drugs, liver function monitoring becomes essential [Gupta et al. (1994) Continuing Medical Education Antigungal Agents: An Overview. Part II, 30:911–33].

Properties of an "ideal" oral antifungal agent most suitable for the treatment of onychomycosis would include favorable nail kinetics, good incorporation into the nail matrix, adequate diffusion through the nail bed, high clinical cure rate, high mycological cure rate, low incidence of relapse, effective when used for short-term therapy, low incidence of side effects, fewer drug interactions with other drugs or food, etc., and cost effectiveness.

Unfortunately, non of the oral anti fungal agents, neither the traditional nor the new generation drugs is ideal because of the potential for significant side effects, drug interaction, high incidence of relapse, long term therapy and high cost.

Light sources, e.g., lasers, xenon lamps, etc., are commonplace in medicine for different applications. For example, lasers are used in surgery for both cutting and cauterization. Other applications use the property of absorption of light energy in order to transfer it to the tissue. One common usage of lasers involve phototherapy, particularly the treatment of tumors of different types by burning. Enhancing light absorption of the tumor enables the efficient transfer of laser energy to it, its heating and finally, its destruction.

In general, special substances that have an efficient absorption coefficient of the light wavelength employed are introduced by various methods into the tissue to be treated. Illuminating (irradiating) the treated area of skin or tissue with an energetic light beam, transfers some of the light energy, preferably most of it, to the light absorbent substance. The substance, which absorbs energy faster than it is lost, is thus heated. Depending on the absorbent substance, the tissue, and the light source properties, the nearby area is also heated. Using the right parameters of light intensity, duration and wavelength with a suitable choice for a light absorber, one can create the desired heating and curing effects in the tissue.

U.S. Pat. Nos. 5,226,907 and 5,425,728 to Tankovich discloses a device and process for the permanent removal of unwanted human hair. Hair is contaminated with a substance which strongly absorbs a specific wavelength of light. The skin is then illuminated by a laser producing light at the specified wavelength and at a sufficient intensity and duration to kill the follicles or the skin tissue feeding the hair. There is however no discussion of pathogens treatment using laser technology.

There is thus a widely recognized need for, and it would be highly advantageous to have, a phototherapy method for treating skin and nail pathogens and a pharmaceutical composition to effect same.

SUMMARY OF THE INVENTION

According to the present invention there is provided a phototherapy based method for treating pathogens, and a pharmaceutical composition for effecting same.

According to further features in preferred embodiments of the invention described below, provided is a method for treating an area of skin or nail affected with a pathogen, the method comprising the step of irradiating the area of skin or nail with a light beam having at least one wavelength absorbable by the pathogen.

According to still further features in the described preferred embodiments the method further comprising the step of causing the pathogen to include a light absorbing substance prior to the irradiation.

According to still further features in the described preferred embodiments the area of skin or nail is of a human being.

According to still further features in the described preferred embodiments causing the pathogen to include the light absorbing substance is effected by ultraviolet irradiation.

According to still further features in the described preferred embodiments causing the pathogen to include the light absorbing substance is effected by subjecting the pathogen to a pigment, the pigment is capable of associating with the pathogen, the pigment, when associated with the pathogen, serves as the light absorbing substance;

According to still further features in the described preferred embodiments subjecting the pathogen to the pigment is effected by topically applying the pigment to the area of skin or nail.

According to still further features in the described preferred embodiments the area of skin or nail is pretreated in order to acquire an open texture prior to the topical application of the pigment.

According to still further features in the described preferred embodiments excess of pigment is removed from the area of skin or nail prior to irradiation.

According to still further features in the described preferred embodiments subjecting the pathogen to the pigment is effected by applying the pigment through the blood system.

According to still further features in the described preferred embodiments subjecting the pathogen to the pigment is effected by orally applying the pigment.

According to still further features in the described preferred embodiments the pigment is capable of specifically binding to the pathogen.

According to still further features in the described preferred embodiments the pigment is conjugated to a substance capable of specifically binding to the pathogen.

According to still further features in the described preferred embodiments the pigment is conjugated to an immunoglobulin or a drug which can specifically bind the pathogen.

According to still further features in the described preferred embodiments the light absorbing material is selected from the group of consisting of lacquer dye, hair dye, India ink, scarlet red, D & C red dyes, toluidine blue, microcyanine, hematoporphyrin derivatives, photophrin II, chlorophyll derivatives, chlorin-E6, black ink, lycopene, carotenoids, 5-aminolaevulic acid, benzoporphyrin derivative monoacid, tetra (m-hydroxyphenyl) chlorin, N-aspartyl chlorine-E6, tinetiopurin, anti-malarials, phenothiazines, clofazimine, minocycline, zinc phthalocyanine derivatives, a combination of photo dynamic therapy with bioreductive drugs, carotene, lycopene, riboflavin, silver, gold, mercury, bismuth, iron, zinc, copper, picric acid, dinitrophenol, iron salts, pararosaniline chloride, acid lost stains, phenol red, carbol fuchsin, $H_2SO_4$, methylene blue, bromcresol, brilliant green, ascospore stain, bromcresol purple, calcofour stain, Evans blue, Giemza stain, Tween 80, gomori methenamine silver stain, gram stain including hucker modification, loctophenol cotton blue, loctophenol cotton blue with polyvinyl alcohol (PVA), bromthymol blue, eosin gentian violet, thiopyronin, phthalocyanine and chloraluminicin.

According to still further features in the described preferred embodiments the light beam is produced by a laser system selected from the group consisting of a dye laser, a ruby laser, a tunable titanium-sapphire laser, a Copper vapor laser, a $CO_2$ laser, an Alexandrite laser, a diode laser, an argon laser, an argon-dye laser, a KTP laser, a krypton laser, an Nd:Yag laser and a doubled Nd:Yag laser.

According to still further features in the described preferred embodiments the area of skin or nail is treated with an anti-irritant subsequent to the irradiation.

According to still further features in the described preferred embodiments causing the pathogen to include the light absorbing substance is effected by subjecting the pathogen to a compound, the compound inducing the pathogen to develop a pigment, the pigment serves as the light absorbing substance.

According to still further features in the described preferred embodiments subjecting the pathogen to the compound is effected by topically applying the compound to the area of skin or nail.

According to still further features in the described preferred embodiments the area of skin or nail is pretreated in order to open prior to the topical application of the compound.

According to still further features in the described preferred embodiments subjecting the pathogen to the compound is effected by applying the compound through the blood system.

According to still further features in the described preferred embodiments subjecting the pathogen to the compound is effected by orally applying the compound.

According to still further features in the described preferred embodiments the compound is a nutrient, such as a hydrocarbon.

According to still further features in the described preferred embodiments the nutrient is dextrose.

According to still further features in the described preferred embodiments the dextrose is cornmeal or potato dextrose.

According to still further features in the described preferred embodiments provided is a method for treating an area of skin or nail affected with a pathogen, the method comprising the steps of (a) infecting the area of skin or nail with a competing pathogen, the competing pathogen including a light absorbing substance; and (b) irradiating the area of skin or nail with a light beam having at least one wavelength absorbable by the light absorbing substance and capable of penetrating the skin or nail.

According to still further features in the described preferred embodiments provided is a composition for use in the treatment of an area of skin or nail affected with a pathogen comprising a light absorbing substance and a pharmaceutically acceptable carrier.

According to still further features in the described preferred embodiments provided is a composition for use in the treatment of an area of skin or nail affected with a pathogen comprising a compound for inducing a pigmentation process in the pathogen and a pharmaceutically acceptable carrier.

According to still further features in the described preferred embodiments the compound is dextrose.

According to still further features in the described preferred embodiments the composition further comprising an agent, the agent affects the skin or nail to have an open texture.

According to still further features in the described preferred embodiments the agent is selected from the group consisting of urea and salicylic acid.

According to still further features in the described preferred embodiments provided is a composition for use in the treatment of an area of skin or nail affected with a pathogen comprising a competing pathogen and an acceptable carrier, the competing pathogen including a light absorbing substance.

According to still further features in the described preferred embodiments provided is a composition for use in the treatment of an area of skin or nail affected with a pathogen comprising a pigment and an acceptable carrier, said pigment being capable of associating with said pathogen.

The present invention successfully addresses the shortcomings of the presently known configurations by providing a reliable, quick and terminal treatment for skin and nail infections with no associated side effects.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of a phototherapy based method for treating pathogens which can be used to heal pathogen associated infections. Specifically, the present invention can be used for treating pathogens, such as, fungi, yeast, bacteria and viruses which cause nail and skin infections. In particular, the present invention can be used for treating onychomycosis caused, for example, by *Trichophyton rubrum*, fungal skin infections, such as, tinea corporis, tinea capitis, tinea barbae, tinea facie (of the face), tinea pedis, tinea manum, tinea cruris and tinea vesicolore and viral skin infection, in particular human papiloma virus (HPV) infection. The present invention if further of a pharmaceutical composition used to effect the method of the invention.

In cases where the treated pathogen is a virus, the term "pathogen" refers both to the virus itself and/or to cells infected with the virus, which under the influence of such infection behave like a parasite.

The principles and operation of the method and composition according to the present invention may be better understood with reference to the drawings and accompanying descriptions.

Thus, the method according to the present invention involves treating an area of skin or nail, e.g., of a human being, affected with a pathogen by irradiating the area of skin or nail with a light beam. The light beam is selected to include at least one wavelength absorbable by the pathogen. As such, should the beam be of an intensity sufficient for at least partially penetrating the skin or nail and to reach the pathogen, the interaction between the light having the specific wavelength and the pathogen would result in exes heating and thereby destruction of the pathogen.

As detailed in the Background section above, some pathogens which are known to affect skin or nail develop a pigment, during at least some life stages, when grown in culture. As a result they form colored colonies. However, most culture pigmented pathogens do not develop pigmentation when growing as parasites in skin or nail tissue. As such, these pathogens lack a light absorbing substance, which renders them substantially indifferent to irradiation as described.

Therefore, according to a preferred embodiment, the method of the present invention further involves a step causing the pathogen to include a light absorbing substance prior to its irradiation by the light beam including the matching wavelength.

As further detailed hereinbelow, according to the present invention three methods can be alternatively employed for causing the skin or nail pathogen to include a light absorbing substance.

According to one embodiment, the pathogen is subjected (exposed) to a pigment capable of association with (e.g., bind to, taken-up by) the pathogen. The pigment, when associated with the pathogen, serves as the light absorbing substance. Association may be, for example, with the cell membrane, cytoplasm and/or nucleus of the pathogen.

Subjecting the pathogen to the pigment may, for example, be effected by topically applying a preparation including the pigment to the treated area of skin or nail. To this end, the pigment is mixed with a pharmaceutically acceptable carrier to form a solution/cream/ointment/gel which penetrates into the skin or nail.

The preparation is preferably placed onto and/or rubbed into the affected skin or nail area and left to interact with the pathogen, preferably, for about 15–30 minutes or more. During this time the pigment migrates through the skin or nail surface to the pathogen, where it remains.

In order to limit the heating effect mostly to the pathogens, as opposed to surrounding tissue, prior to irradiation the excess carrier and pigment left on the skin or nail surface is subsequently removed using a standard cleaning solution or a pad.

In order to improve the penetration of the pigment through the skin or nail tissue, the treated area of skin or nail is preferably pretreated in order to render its texture open, prior to the topical application of the pigment.

However, subjecting the pathogen to the pigment may alternatively be systemic, for example, by applying the pigment through the blood system of the treated individual, e.g., intravenously using an i.v. solution as a carrier, or orally, provided that they are resistant to digestion effects imposed by the digestion system and may transfer to the blood system.

A pigment suitable for systemic application is, for example, giseofulvin, ketocnazole, fluconazole, itraconazole and allylamines or their derivatives conjugated to a pigment, since these substances are known to accumulate in the nails.

In addition, there are drugs which are used to treat various non-related conditions which are known to induce nail pigmentation as a side effect. One example are the antimalarial drugs chloroquine (aralene), quincrine and amodiaquine, which induce a blue-brown nail pigmentation, due to melanin-antimalarial drug complexes deposition in the nail bed and plate. Another example is minocycline used to treat acne vulgaris which induce a blue nail pigmentation due to iron-drug complexes deposition. Other examples are listed in Fitz Patrick et al. (1993) Dermatology in General Medicine. McGraw-Hill, N.Y., p. 704. Such a drug may therefore serve as a carrier for the pigment to reach specifically to the nail. However, the phenomenon of drug associated nail pigmentation may serve per se for providing a light absorbing substance according to the invention.

Oral application may be effected either by tablets, capsules, suppositories, etc., all as well known in the art.

Systemic and/or topic application may further be effected via an implant device or active pad device, or by any other method known in the art.

The pigment is preferably selected capable of specifically binding to the pathogen, e.g., binding in high affinity to the membrane of the pathogen or taken-up (e.g., active uptake) by the pathogen.

Toluidine blue, eosin and hematoporphyrin are well known pigments that accumulate in the plasma membrane of yeast cells and may therefore be used according to the present invention as suitable pigments to treat yeast skin and nail infections.

For example, topically applying a solution containing 20% hematoporphyrin derivatives and 40% urea to the skin nail, removing access pigment and irradiating the yeast affected region of skin or nail with argon-dye laser at 632 nm with an energy of about 5–10 $J/cm^2$ would result in complete destruction of the yeast cells due to heat production. Other dyes, such as acridine orange, which tend to accumulate in the cytoplasm and/or nucleus may also be used.

A pigment incapable of specifically binding the pathogen may be made specific by having it conjugated to an immunoglobulin or drug which is specific to that pathogen. Anti-Trichophyton sp., anti-Candida sp., anti Aspergillaceae sp. mono- and polyclonal antibodies are available from Ecopath Aspergillus, Institute Pasteur, Genk, Belgium. Antibodies specific for other pathogens are also available. If the pathogen corresponding to the antibody applied is present, it will be labeled, and rendered pigmented by, for example, direct immunofluorescence, immunoperoxidase reaction, or avidin-biotin complex formation methods, as well known in the art.

One ordinarily skilled in the art would know how to conjugate various pigments to various immunoglobulins and/or drugs without affecting the specific binding capabilities of the latters and the pigment characteristics of the former.

Thus, according to the present invention the pigment may be a dye, a drug or any substance which absorbs light at a desired wavelength.

Examples of dyes which can be used to implement the method of the present invention include lacquer dye, hair dye (deep black and blue), India ink, scarlet red, D & C red dyes, toluidine blue, microcyanine, hematoporphyrin derivatives, photophrin II, chlorophyll derivatives, chlorin-E6, black ink, lycopene and carotenoids (e.g., β carotene).

For example, the light absorption of bacterial chlorophyll peaks at 770, 573, 392 and 357 nm. The light absorption of chlorophyll A peaks at 660, 613, 577, 532, 428, 408 and 377 nm. The light absorption of lycopen peaks at 457, 484 and 520 nm. Whereas, the light absorption of β carotene peaks at 466 and 494 nm.

Examples of drugs which can be used include 5-aminolaevulic acid (ALA), benzoporphyrin derivative monoacid, tetra (m-hydroxyphenyl) chlorine, N-aspartyl chlorine-E6, tinetiopurin, anti-malarials, phenothiazines, clofazimine, minocycline (tetracycline), zinc phthalocyanine derivatives and a combination of photo dynamic therapy (PDT) with various bioreductive drugs.

Further substances which can be used as pigments according to the present invention include vitamins such as carotene, lycopene and riboflavin; metals such as silver, gold, mercury, bismuth, iron, zinc and copper; chemical compounds such as picric acid and dinitrophenol (DNP); and therapeutic agents such as iron salts and Gentian violet (pararosaniline chloride).

Further substances which can be used as pigments are stains typically used for histopathological staining of pathogens such as fungi. These include acid lost stains which stain pink to red; phenol red, carbol fuchsin, $H_2SO_4$, methylene blue, bromcresol, brilliant green, ascospore stain, bromcresol purple, calcofour stain, Evans blue, Giemza stain, Tween 80, gomori methenamine silver stain, gram stain including hucker modification, loctophenol cotton blue, loctophenol cotton blue with polyvinyl alcohol (PVA), bromthymol blue, eosin gentian violet, thiopyronin, phthalocyanine and chloraluminicin. These stains are presently used for staining various pathogen samples before microscope examination.

According to another embodiment of the invention, causing the pathogen to include the light absorbing substance is effected by subjecting the pathogen to a compound which induces the pathogen to develop an endogenous pigment, the induced pigment serves as the light absorbing substance. The compound may, for example, be applied topically to the treated area of skin or nail. In order to improve the penetration of the compound through the skin or nail tissue, the treated area of skin or nail is preferably pretreated in order to render its texture open prior to the topical application of the compound.

Depending on its nature and the specific pathogen to be treated, the compound may also by applied systematically via the blood system (e.g., intravenously or orally).

The pigmentation inducing compound may be a nutrient such as a hydrocarbon. For treating nail onychomycosis cased by, for example, *Trichophyton rubrum*, the preferred nutrient is dextrose, most preferably, cornmeal or potato dextrose, since cornmeal or potato dextrose induces this species to develop red to brownish-red pigmentation both in culture and in nail, as further detailed in the Examples section below. Interestingly, *Trichophyton rubrum* infected nails of diabetic individuals tend to develop a reddish color.

Further nutritional substances which can be used to induce pigment production are selected substances used in media prepared for mycology, or the media itself. Compositions of various media used for mycology are described in Larone (1993) Medically Impotant Fungi a Guide to Identification. American Society for Microbiology, which is incorporated by reference, as if fully set forth herein.

As mentioned above, in preferred embodiments, the treated area of skin or nail is pretreated in order to form an open texture prior to the topical application of the compound or pigment, such that the compound or pigment topically applied is allowed to better penetrate the skin or nail tissue and reach the pathogen.

Pretreating the treated area of skin or nail may include (a) topical application of a composition containing an agent such as urea, salicylic acid or any other equivalently active compound; and (b) steam therapy.

A treatment performed concurrent to the application of the compound or pigment, such as (a) topical application of a composition containing urea, salicylic acid or any other equivalently active compound; (b) steam therapy; and (c) active transdermal delivery, such as, iontophoresis, ultrasound or electroporation, may also be used to enhance penetration.

Active transdermal delivery is well known in the art. Few strategies are employed for transdermal active drug delivery via active pads.

Iontophoresis, is employed to deliver small charged molecules across the skin. In this case, the molecules follow a path dictated by their self charge and the charge imposed on the pad by a power source.

Electroporation employs short and strong pulses of electricity to create temporary openings in the skin through which large molecules can pass.

Ultrasound employs high-pitched sound to temporarily disrupt the skin's structure, creating microscopic holes through which large molecules can pass.

Further details concerning the functionality and precise construction of active pads are well known in the art. Such details are found, for example, in "Breaking the skin barrier" (1996) by Ingrid Wickelgren, Popular Science, December, pp. 86–89; "Controlled drug delivery fundamentals and applications" Second edition (1987) J. R. Robinson and V. H. L. Lee editors, Marceldekker Inc. New York, and U.S. Pat. Nos. 5,169,384; 4,763,660; 5,443,441 and 3,447,537, all are incorporated by reference as if fully set forth herein.

According to yet another embodiment of the invention, causing the pathogen to include the light absorbing substance is effected by subjecting the pathogen to ultraviolet (UV) irradiation, such as UVA radiation (wavelength range ca. 320–400 nm). UVA irradiation may be effected by a suitable UV source or by sunlight. Interestingly, *Trichophyton rubrum* infected nails which are exposed to sunlight tend to develop a reddish color.

Brash and Menz in their article "UV Susceptibility and Negative Phototropism of Dermatophytes" (1995) Mycoses 38:197–203, reported that *Trichophyton rubrum* was unaffected by infrared irradiation but responded with increased pigmentation to UVA irradiation.

A sunlight induced pigmentation of *Trichophyton rubrum* is reported by Goetz in Handbuch der Haut-und Geschlechtskrankheiten Ergaenzungswerk Band IV Teil 3 (1962) Berlin. Springler, pp. 112–19. See also Fitz Patrick et al. (1993) Dermatology in General Medicine. McGraw-Hill, New York, pp. 1627–38.

Some pathogens are more suited to flourish as parasites than others. Therefore, should an area of skin or nail which is affected by any given pathogen will be infected by a second, competing, pathogen than, if the competing pathogen is selected more suited to flourish, such a competing pathogen will eventually replace the original pathogen, since, for example, both compete for limited resources such as space and nutrients. Should the competing pathogen be selected a pigmented pathogen, than following infection it could be treated as described by irradiation.

Thus, the original pathogen is eliminated by the competing pathogen, whereas the second pathogen is destroyed via irradiation. The competing pathogen may be acquired an additional relative advantage, by treating the first pathogen with a conventional agent which does not affect the competing pathogen.

Therefore, according to another embodiment of the invention, the method for treating an area of skin or nail affected with a pathogen includes: first, infecting the area of skin or nail with a competing pathogen, the competing pathogen includes a light absorbing substance; and than, irradiating the area of skin or nail with a light beam having at least one wavelength absorbable by the light absorbing substance and capable of penetrating the skin or nail. The competing pathogen is either natively pigmented, artificially colored or induced to develop a pigment (e.g., in culture prior to infection).

Regardless of the method employed to have the pathogen include a light absorbing substance, the irradiating light beam is selected to include at least one wavelength absorbable by the pathogen and it is preferably acquired an intensity sufficient for penetrating the skin or nail and reach the pathogen, such that the interaction between the light and the pathogen would result in exes heating and destruction of the pathogen.

In a preferred embodiment of the invention the light beam is a laser beam, and most preferably a pulsed laser beam. Several different laser systems may be applicable for implementing the method of the present invention, and the choice of each should depend upon the choice of the appropriate light absorbent substance and vice versa.

As an example consider the use of hair dye (deep black and blue) with a dye laser (587 nm) or copper vapor laser (578 nm) or doubled Nd:Yag (532 nm) laser. Alternatively, India ink can be used along with the Nd:Yag laser (1,064 nm) system.

The laser system chosen must fulfill two principal requirements: (a) the light beam produced by the system penetrates the skin relatively easily; and (b) it is well absorbed by the light absorbing substance, such that excessive heating is generated.

Several laser systems are applicable in the view of these demands. A partial list is summarized in the following table:

TABLE 1

Laser Systems and Corresponding Absorbing Substances

| Laser System | Pigment |
| --- | --- |
| Copper vapor (512 nm, 578 nm) green/yellow | Microcyanine |
| Argon - dye (640 nm) - red | Hematoporphyrin derivatives, Photophrin II, Chlorophyll derivatives |
| Dye (660 nm) - red | Chlorin-E6, Chlorophyll derivatives |
| Ruby (694 nm) - red | Black ink |
| Tunable Titanium - Sapphire - green and red | all of the above |
| Pigmented lesion dye (500–520 nm) green | Lycopene, carotenoids |

Other general laser systems which may be used include $CO_2$, alexandrite, diode, argon, KTP and krypton lasers.

The choice of the appropriate laser system and related light absorbing substance will be clear to those who are skilled in the art.

For example, a pulsed Ruby laser with pulse widths of about 100 ns or a Dye laser with a duration of pulses of about 150 ms may be used, using a beam cross-section diameter of about 0.4 cm and energy density of about 1.5–6.5 $J/cm^2$.

Thus, laser systems suitable of generating an appropriate light beam include, but are not limited to, a dye laser, a ruby laser, a tunable titanium-sapphire laser, a copper vapor laser, a $CO_2$ laser, an Alexandrite laser, a diode laser, an argon laser, an argon-dye laser, a KTP laser, a krypton laser, an Nd:Yag laser and a doubled Nd:Yag laser.

Details concerning the various laser systems, their wavelengths, etc., are found in Siegman (1986) "Lasers". University Science Books; and Yariv (1991) "Optical Electronics". Saunders College Publishing, Fourth Edition; both are incorporated by reference as if fully set forth herein.

An alternative embodiment is the use of a non-coherent light source with a wider band width, e.g. a xenon lamp. Due to their band width, such light sources provide a more flexible choice of light absorbing substance, they are cost effective and they offer the possibility of home usage by the patient in certain cases.

In any case, due to the light absorbing substance present in the pathogen, irradiating results in excessive heat production which leads to the destruction of the pathogen and therefore to the termination of the infection condition.

Examples of pathogens which may be treated according to the method of the present invention are given hereinbelow.

The characteristic green color of the nail seen in bacterial infection caused by the bacterium *Pseudomonas aeruginsa* is seen in FIGS. 3.16 and 3.17, In: "The Nails in Disease" (1995) by Samman and Fenton. Butterworth-Heinemann Ltd. Linacre House, Jordan Hill, Oxford, Fifth Edition.

It is known that culturing *Pseudomonas aeruginsa* results in production of two pigments, the yellow fluorescein and the blue pyocyanin. A special media for enhancing pigment production in *Pseudomonas aeruginsa* sabouraud maltose agar. A preparation containing maltose may therefore prepared and used to induce pigmentation.

Thus, if the pigment is fluorescein the nail will be irradiated with a laser pulsed at a wavelength absorbable by fluorescein having an emmitance peaking at 525 nm. To this end, preferred laser sources are HeCd (441 nm) and Er:Glass (1.54 $\mu s$) tripled to 513 nm. Other sources with wavelengths from 370 nm to 520 nm would be satisfactory. Preferred power levels are between 5 to 15 $J/cm^2$ depending on nail thickness, fluorescein metabolism, etc. Preferred pulse duration is about 1 $\mu s$ or less.

The mite *Sarcoptes scabiei* belonging to the order Acari usually spreads by skin-toxin contact, tunneling the epidermis and depositing its eggs. The infestation is a common problem world wide. In this case, the tunnels thus formed may be filled up with a pigment, such as, but not limited to, a solution of 2–5% disodium fluorescein by topically applying the pigment to the skin. The pigment solution is absorbed into the tunnels formed by the mite by capillary action. The skin is thereafter cleaned thoroughly from access of pigment. Next the skin is irradiated with a suitable irradiation absorbable by the pigment used.

After having treated the affected area of skin, the patient is recommended to avoid sun exposure for about a month, as well as to use sun blockers to prevent inflammation. The patient is also recommended to use a topical antibiotic ointment, gel, or cream. For local irritation, the use of steroids, topical or systemic anti-histamine, or other contra-irritant agents (e.g. Aloevera) is recommended.

Further according to the present invention provided is a composition for use in the treatment of an area of skin or nail affected with a pathogen. According to one embodiment the composition includes a light absorbing substance, e.g., one of the pigments listed above, and a pharmaceutically acceptable carrier.

According to another embodiment the composition includes a compound for inducing a pigmentation process in the pathogen and a pharmaceutically acceptable carrier. In a preferred embodiment the compound is a nutrient used in mycology growth media, such as dextrose (e.g., potato or cornmeal dextrose) and maltose.

The composition according to any of the above two embodiments preferably further includes an agent directed at opening the texture of the skin or nail e.g., urea, salicylic acid or any other equivalently active agent.

According to still another embodiment, the composition includes a competing pathogen and an acceptable carrier, the competing pathogen includes a light absorbing substance.

Reference is now made to the following examples, which together with the above descriptions, illustrate the invention in a non limiting fashion.

EXAMPLE 1

Figure 2:
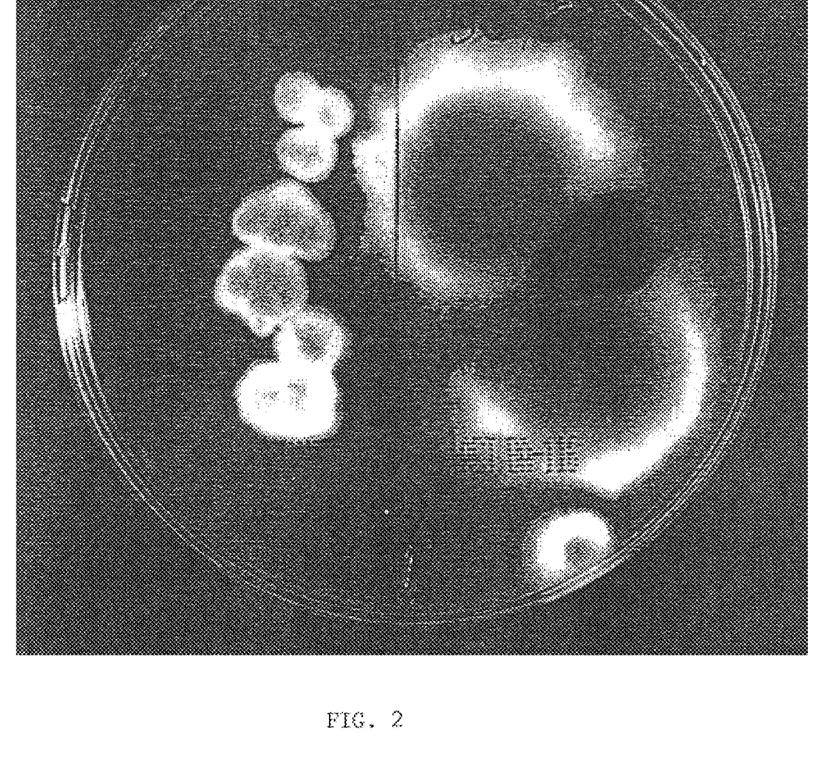
FIG. 2 is a photograph of culture grown *Trichophyton rubrum* (big dark colonies on the right) and *Trichophyton mentagrophytes* (small lighter colonies on the left periphery) colonies presenting an intense red color when reversed.

*Trichophyton Rubrum* and *Trichophyton mentagrophytes* were cocultured on a sabouraud dextrose agar (SDA) medium containing 20 grams dextrose, 10 grams peptone and 17 grams agar per 1,000 ml distilled water, final pH 6.9, for 4 weeks at 26° C. The surface of both colonies is fluffy white to buff. As shown in FIG. 2, reverse of *Trichophyton Rubrum* is deep red to black-brown, whereas reverse of *Trichophyton mentagrophytes* is yellow in the periphery and tan-brown in the center.

EXAMPLE 2

A male patient suffering from a relapsed condition of onychomycosis caused by *Trichophyton rubrum* in few of his toe nails was treated with a composition according to the present invention.

To this end, the patient's big toe nail was treated with a preparation containing:

Urea 40%
Anhydrous Lanolin 20%
White Wax 5%
White Petrolatum 35% for three successive nights, by applying the preparation to the nail and covering the nail with a band-aid.

Thereafter, the nail was treated with a second preparation containing:

Urea 35%
Anhydrous Lanolin 20%
White Wax 5%
White Petrolatum 35%
Potato Dextrose Agar 5% under otherwise similar conditions. Potato Dextrose Agar was from Bacto Dickson and Company Cockeysville Md. 21030 USA.

Following fourteen days, the big toe nail of the patient developed a brownish-red color. Other affected nails remained unchanged.

While the invention has been described with respect to a limited number of embodiments, it will be appreciated that many variations, modifications and other applications of the invention may be made.

What is claimed is:

1. A method for treating an area of skin or nail infected with a fungal pathogen, the method comprising the steps of causing said fungal pathogen to include a light absorbing substance and irradiating the area of skin or nail with a light beam having at least one wavelength absorbable by said light absorbing substance, wherein said light absorbing substance and said light beam having said at least one wavelength absorbable by said light absorbing substance are selected such that an interaction between said light beam having said at least one wavelength absorbable by said light absorbing substance and said light absorbing substance results in excessive heating, which, by itself, is sufficient for destruction of the fungal pathogen.

2. The method of claim 1, wherein the area of skin or nail is of a human being.

3. The method of claim 1, wherein causing said fungal pathogen to include said light absorbing substance is effected by induction via ultraviolet irradiation.

4. The method of claim 1, wherein causing said fungal pathogen to include said light absorbing substance is effected by subjecting said fungal pathogen to a pigment, said pigment is capable of associating with said fungal pathogen, said pigment, when associated with said fungal pathogen, serves as said light absorbing substance.

5. The method of claim 4, wherein subjecting the fungal pathogen to said pigment is effected by topically applying said pigment to the area of skin or nail.

6. The method of claim 5, wherein the area of skin or nail is pretreated in order to acquire an open texture prior to said topical application of said pigment.

7. The method of claim 5, wherein excess of pigment is removed from the area of skin or nail prior to irradiation.

8. The method of claim 4, wherein subjecting the fungal pathogen to said pigment is effected by applying said pigment through the blood system.

9. The method of claim 4, wherein subjecting the fungal pathogen to said pigment is effected by orally ingesting said pigment.

10. The method of claim 4, wherein said pigment is capable of specifically binding to the fungal pathogen.

11. The method of claim 10, wherein said pigment is conjugated to a substance capable of specifically binding to the fungal pathogen.

12. The method of claim 11, wherein said pigment is conjugated to an immunoglobulin or a drug which can specifically bind the fungal pathogen.

13. The method of claim 1, wherein said light absorbing material is selected from the group of consisting of lacquer dye, hair dye, India ink, scarlet red, D & C red dyes, toluidine blue, microcyanine, hematoporphyrin derivatives, photophrin II, chlorophyll derivatives, chlorin-E6, black ink, lycopene, carotenoids, 5-aminolaevulic acid, benzoporphyrin derivative monoacid, tetra (m-hydroxyphenyl) chlorin, N-aspartyl chlorine-E6, tinetiopurin, anti-malarials, phenothiazines, clofazimine, minocycline, zinc phthalocyanine derivatives, a combination of photo dynamic therapy with bioreductive drugs, carotene, lycopene, riboflavin, silver, gold, mercury, bismuth, iron, zinc, copper, picric acid, dinitrophenol, iron salts, pararosaniline chloride, acid lost stains, phenol red, carbol fuchsin, $H_2SO_4$, methylene blue, bromcresol, brilliant green, ascospore stain, bromcresol purple, calcofour stain, Evans blue, Giemsa stain, Tween 80, gomori methenamine silver stain, gram stain including hucker modification, loctophenol cotton blue, loctophenol cotton blue with polyvinyl alcohol (PVA), bromthymol blue, eosin gentian violet, thiopyronin, phthalocyanine and chloraluminicin.

14. The method of claim 1, wherein said light beam is produced by a laser system selected from the group consisting of a dye laser, a ruby laser, a tunable titanium-sapphire laser, a Copper vapor laser, a $CO_2$ laser, an Alexandrite laser, a diode laser, an argon laser, an argon-dye laser, a KTP laser, a krypton laser, an Nd:Yag laser and a doubled Nd:Yag laser.

15. The method of claim 1, wherein the area of skin or nail is treated with an anti-irritant subsequent to said irradiation.

16. The method of claim 1, wherein causing said fungal pathogen to include said light absorbing substance is effected by subjecting said fungal pathogen to a compound, said compound inducing said fungal pathogen to develop a pigment, said pigment serves as said light absorbing substance.

17. The method of claim 16, wherein subjecting the fungal pathogen to said compound is effected by topically applying said compound to the area of skin or nail.

18. The method of claim 16, wherein the area of skin or nail is pretreated in order to open prior to said topical application of said compound.

19. The method of claim 16, wherein subjecting the fungal pathogen to said compound is effected by applying said compound through the blood system.

20. The method of claim 16, wherein subjecting the fungal pathogen to said compound is effected by orally ingesting said compound.

21. The method of claim 16, wherein said compound is a nutrient.

22. The method of claim 21, wherein said nutrient is dextrose.

23. The method of claim 22, wherein said dextrose is cornmeal or potato dextrose.

* * * * *

UNITED STATES PATENT AND TRADEMARK OFFICE
CERTIFICATE OF CORRECTION

PATENT NO.    : 6,090,788
DATED         : July 18, 2000
INVENTOR(S)   : Lurie

It is certified that error appears in the above-identified patent and that said Letters Patent is hereby corrected as shown below:

<u>Title page,</u>
Please add to "Related U.S. Application":

-- U.S. Patent Application Serial No. 08/901,426, filed July 28, 1997 --

Signed and Sealed this

Eighteenth Day of June, 2002

Attest:

Attesting Officer

JAMES E. ROGAN
*Director of the United States Patent and Trademark Office*